(12) United States Patent
Rajapandian et al.

(10) Patent No.: US 11,260,008 B2
(45) Date of Patent: Mar. 1, 2022

(54) HAIR TREATMENT COMPOSITION

(71) Applicant: Conopco, Inc., Englewood Cliffs, NJ (US)

(72) Inventors: Benjamin Jesukumar Rajapandian, Chester (GB); Stephen Robert Ricketts, Leicester (GB); Glyn Roberts, Wirral (GB)

(73) Assignee: Conopco, Inc., Englewood Cliffs, NJ (US)

( * ) Notice: Subject to any disclaimer, the term of this patent is extended or adjusted under 35 U.S.C. 154(b) by 0 days.

(21) Appl. No.: 16/329,650

(22) PCT Filed: Sep. 22, 2017

(86) PCT No.: PCT/EP2017/074021
§ 371 (c)(1),
(2) Date: Feb. 28, 2019

(87) PCT Pub. No.: WO2018/065237
PCT Pub. Date: Apr. 12, 2018

(65) Prior Publication Data
US 2019/0192403 A1 Jun. 27, 2019

(30) Foreign Application Priority Data
Oct. 5, 2016 (EP) .................................. 16192472

(51) Int. Cl.
| | | |
|---|---|---|
| A61K 8/44 | (2006.01) | |
| A61Q 5/00 | (2006.01) | |
| A61K 8/46 | (2006.01) | |
| A61K 8/41 | (2006.01) | |
| A61K 8/49 | (2006.01) | |

(52) U.S. Cl.
CPC ............... *A61K 8/44* (2013.01); *A61K 8/416* (2013.01); *A61K 8/46* (2013.01); *A61K 8/463* (2013.01); *A61K 8/4913* (2013.01); *A61Q 5/002* (2013.01); *A61K 2800/5922* (2013.01)

(58) Field of Classification Search
CPC .......... A61K 8/44; A61K 8/416; A61K 8/463; A61K 8/4913; A61Q 5/002
See application file for complete search history.

(56) References Cited

U.S. PATENT DOCUMENTS

| | | | |
|---|---|---|---|
| 4,201,235 A | 6/1980 | Ciavatta | |
| 4,906,460 A | 6/1990 | Kim et al. | |
| 5,559,092 A * | 9/1996 | Gibson | A61K 8/44 |
| | | | 132/202 |
| 7,429,561 B2 | 9/2008 | Nakamura et al. | |
| 8,642,659 B2 * | 2/2014 | Springer | A61K 8/43 |
| | | | 514/634 |
| 8,795,643 B1 | 5/2014 | Anthony | |
| 2002/0035046 A1 | 3/2002 | Lukenbach et al. | |
| 2007/0081967 A1 | 4/2007 | Cerullo et al. | |
| 2008/0058400 A1 | 3/2008 | Yang et al. | |
| 2011/0117219 A1 * | 5/2011 | Springer | A61K 8/43 |
| | | | 424/728 |
| 2014/0158148 A1 * | 6/2014 | Mette | A61K 8/416 |
| | | | 132/202 |
| 2015/0174038 A1 * | 6/2015 | Krueger | A61K 8/39 |
| | | | 132/202 |
| 2015/0272860 A1 * | 10/2015 | Mette | A61K 8/44 |
| | | | 132/202 |
| 2015/0272865 A1 | 10/2015 | Mette et al. | |
| 2019/0060199 A1 | 2/2019 | Suzuki et al. | |

FOREIGN PATENT DOCUMENTS

| | | | | |
|---|---|---|---|---|
| CH | 697229 | | 7/2008 | |
| CN | 101692996 | | 4/2010 | |
| CN | 106580722 | A * | 4/2017 | ............... A61K 8/44 |
| EP | 1142904 | | 10/2001 | |
| EP | 1342474 | A1 * | 9/2003 | ............... A61K 8/44 |
| EP | 2886162 | | 6/2015 | |
| FR | 2853531 | | 10/2004 | |
| FR | 2939198 | | 6/2010 | |
| GB | 720561 | | 12/1954 | |
| GB | 987800 | | 3/1965 | |
| JP | H1087444 | | 4/1998 | |
| JP | 2007031305 | | 2/2007 | |
| JP | 2011042588 | | 3/2011 | |
| JP | 2014214150 | | 11/2014 | |
| WO | WO0051556 | | 9/2000 | |
| WO | WO2012031069 | | 3/2012 | |
| WO | WO2013081193 | | 6/2013 | |
| WO | WO2013168803 | | 11/2013 | |
| WO | WO2014090513 | | 6/2014 | |

(Continued)

OTHER PUBLICATIONS

Oshimura, et al. Hair and amino acids: The interactions and the effects. J. Cosmest. Sci., 58:347-357 (Year: 2007).*
Trueb. The impact of oxidative stress on hair. International Journal of Cosmetic Science, 37 (Suppl. 2), 25-30 (Year: 2015).*
Robins. Chemical and Physical Behavior of Human Hair. Ed. Springer. Chapter 2: Chemical Composition of Different Hair Types. pp. 105-176. (Year: 2012).*
Search Report & Written Opinion in EP16192482 dated Dec. 13, 2016.
Search Report and Written Opinion in EP16192482.4 dated Nov. 25, 2016.
Search Report and Written Opinion in PCT/EP2017/074021 dated Oct. 30, 2017.

(Continued)

*Primary Examiner* — Robert A Wax
*Assistant Examiner* — Olga V. Tcherkasskaya
(74) *Attorney, Agent, or Firm* — Foley & Lardner LLP

(57) ABSTRACT

A hair treatment composition comprising (a) from 0.01 to 10 wt % of surfactant in a solvent, by weight of the total composition, and (b) a mixture of amino acids, wherein the mixture of amino acids comprises glutamic acid, alanine and proline gives damage repair benefits to chemically damaged hair.

13 Claims, No Drawings

(56) References Cited

FOREIGN PATENT DOCUMENTS

| WO | WO2014202655 | 12/2014 |
| WO | WO2017188279 | 11/2017 |

OTHER PUBLICATIONS

Search Report and Written Opinion in PCT/EP2017/074177 dated Oct. 30, 2017.
IPRP1 in PCTEP2017074177; Apr. 9, 2019; World Intellectual Property Org. (WIPO).
IPRP1 in PCTEP2017074021; Apr. 9, 2019; World Intellectual Property Org. (WIPO).
Shoaib Arif; The Formulation Basics for Personal Cleansers; HAPPI; Feb. 9, 2009; PP1-11; Pilot Chemical Co.; United States of America.
Qiu et al.; Modern Cosmetic Science and Technology; China Light Industry Press; Mar. 2016; pp. 1293, 1537-1538 with partial English translation.
Zhao Hongbo et al.; Colloid and Surface Chemistry Theory and Application Research; Heilongjiang University Press; Mar. 2016; pp. 52-53, with partial English translation; China.
Clariant; Genamin BTLF; Product Fact Sheet; May 31, 2013; pp. 1-3, Retrieved from the Internet URL: https://www.knowde.com/stores/clariant/products/genamin-btlf.

* cited by examiner

HAIR TREATMENT COMPOSITION

CROSS REFERENCE TO RELATED APPLICATIONS

The present application is a U.S. National Phase Application under 35 U.S.C. § 371 of International Application No. PCT/EP2017/074021 filed on Sep. 22, 2017, which claims priority to European patent application No. 16192472.5 filed on Oct. 5, 2016, the contents of which are incorporated herein in their entireties.

FIELD OF INVENTION

The present invention relates to a dilute surfactant composition, for the treatment of hair, comprising mixtures of amino acids, its use to mitigate the effect of chemical assaults, and a method of treating chemically damaged hair using said composition.

BACKGROUND AND PRIOR ART

Hair is composed mainly of proteins, specifically keratins. Healthy hair has healthy proteins, whilst damaged hair has damaged proteins, depending on the extent and type of damage. Loss of protein and protein substituents, such as amino acids, is characteristic of damaged hair. The denaturation temperature of hair is a reliable indicator of the level of damage and loss of its constituent proteins. The damage to hair protein is reflected in a reduction in the denaturation temperature of the proteins. Once hair is damaged, it is more susceptible to further loss of proteins and therefore to further reduction of hair integrity and to further damage.

Hair is subjected to a range of "assaults" during everyday life or as part of a normal hair care regime or consumer habit. These include chemical assaults (for example, bleaching treatments, colouring treatments and use of surfactants). These assaults damage the hair structure and proteins.

This damage is manifested in numerous ways, including surface damage, chipped scales, lifted scales, loss of shine, loss of smoothness, hair breakage, split ends, cuticle damage and loss, and difficultly in styling. In addition, damaged hair is more porous, which means that it is weaker, more prone to breakage, frizzy fly-away and more susceptible to further damage. There is a need to mitigate these effects.

Treatments are known which address the problem of hair damage due to chemical hair treatments, and which may involve the use of amino acids.

EP 2 886 162A (Henkel) discloses a hair treatment agent containing a homopolymer or copolymer (comprising a vegetable oil monomer), a quaternary ammonium compound and an ester oil. It can also contain at least one amino acid. The composition aims to improve physical damage caused by grooming and blow-drying, and particularly to improve split ends or hair breakage. Damage caused by repeated hair treatments, such as oxidative or reductive hair treatments, as well as the too frequent cleansing of the hair, the action of heat during drying and environmental factors and/or mechanical effects, which can hair defraud in their structure, is also referred to.

WO 14/202655 (L'Oreal) discloses a composition for treating keratin fibres comprising a combination of an acrylic polymer particles, a silicone block copolymer and at least one amino acid or amino acid derivative. The composition effectively coats the hair and is persistent with respect to shampooing and to the various attacking factors to which the hair may be subjected, especially blow-drying and perspiration, while at the same time showing better tolerance towards fatty substances such as sebum without developing any tacky nature.

US 2015/272860 (Henkel) discloses a hair treatment composition including at least one amino acid and/or at least one oligopeptide and/or at least one cationic protein hydrolysate and a sugar structure-containing silicone. The composition aims to reduce the side effects of environmental influences and of oxidative and surfactant hair treatments, preferably during the oxidative and surfactant hair treatments.

WO 14/090513 (Henkel) discloses a composition for treating keratin fibres, without causing dryness and split ends, comprising quaternary ammonium compound, odoriferous substance, a zwitterionic or amphoteric surfactant and a silicone containing sugar structure. The compositions can include amino acids.

WO 12/031069 (Zotos Int Inc) discloses a treatment composition comprising a mixture of peptides made of any of serine, tyrosine, arginine, threonine, glycine, valine, phenylalanine, cysteine and leucine in the sequences identical to human hair keratin proteins; the composition aims to benefit hair strength, manageability and overall conditioning and can be substantive to hair using natural amino acids.

US 2008/058400 (Fujifilm) discloses a skin preparation that comprises at least arginine, aspartic acid, isoleucine, leucine, lysine, threonine, glycine, histidine, serine, valine, tyrosine, cysteine, phenylalanine, hydroxyproline and acyl-glutamine among amino acids, or salts thereof. It can be used as a face lotion, an emulsion, a cream, a hair tonic or a pack.

FR 2 853 531A (Sephytal) discloses an after-shampoo composition containing a mixture of free amino-acids identical with those in human hair and a quaternary amine salt with a 22C fatty chain of the behenyl type, derived from natural colza oil. The amino acids comprise glutamic acid, arginine, proline, aspartic acid, leucine, phenylalanine, serine, lysine, glycine, valine, tyrosine, isoleucine, alanine, threonine, histidine, methionine and cystine. The composition aims to confer to dry hair very dry, damaged or embrittled hair, a better ease of disentangling after washing and rinsing the hair, a gentle significantly improved breath-ability and more shine.

WO 00/51556 (P&G) discloses a hair care composition comprising four or more amino acids where each amino acid is selected from a different group of amino acids. The composition aims to treat hair that is subjected to a wide range of insults that can cause weakening and damage. There remains a need for more effective treatments for damaged hair, which deliver repair benefits during every day hair-care regimes.

"Micellar water" is a dispersion of micelles in a solvent, usually water. Typically, the micelles are formed from mild surfactants at low concentrations.

We have now found that a mixture of specific amino acids, namely glutamic acid, alanine and proline, can repair damage to hair that has been chemically damaged, as evidenced by an increase in the denaturation temperature of the hair. We have surprisingly found that the amino acids mixture of the invention act unusually quickly to repair hair damage by increasing the denaturation temperature of the hair. The compositions of the invention provide repair benefits after just one treatment and can return the denaturation temperature of 8 times bleached hair to that of virgin hair after only 3 treatments. We have surprisingly found that delivery of the amino acids is particularly effective from a dilute surfactant composition.

Specific Description of the Invention

In a first aspect of the invention there is provided a hair treatment composition comprising:

(a) from 0.01 to 10 wt %, preferably from 0.5 to 2.5 wt % of surfactant in a solvent, by weight of the total composition, and (b) a mixture of amino acids, wherein the mixture of amino acids comprises glutamic acid, alanine and proline.

In a second aspect of the invention there is provided a method of treating chemically damaged hair comprising the step of applying to the hair a treatment composition as defined in the first aspect of the invention.

In a third aspect there is provided a use of a composition as defined in the first aspect to repair chemically damaged hair.

General Description

The Composition

The Mixture of Amino Acids

The amino acid mixture for use the compositions of the invention comprises, glutamic acid, alanine and proline. The mixture is preferably free from other amino acids.

The amount of the amino acid mixture in the composition of the invention is preferably from 0.1 wt % to 10 wt %, more preferably from 0.2 wt % to 5 wt %, most preferably from 0.25 wt % to 2 wt %, by total weight of the composition.

The weight ratio of glutamic acid:alanine:proline is preferably 2:1:1 to 1:2:1 to 1:1:2, more preferably 1:1:1.

Amino acids, including glutamic acid, alanine and proline, suitable for use in the invention are available from many suppliers, for example Kusuma Pharma and Ajinomoto co Inc.

The Surfactant in Solvent

In the present invention, the hair treatment composition comprises a surfactant in a solvent.

Suitable surfactants for use in the compositions of the invention are those that are cosmetically acceptable and suitable for topical application to the hair.

Examples of suitable anionic cleansing surfactants are the alkyl sulphates, alkyl ether sulphates, alkaryl sulphonates, alkanoyl isethionates, alkyl succinates, alkyl sulphosuccinates, alkyl ether sulphosuccinates, N-alkyl sarcosinates, alkyl phosphates, alkyl ether phosphates, and alkyl ether carboxylic acids and salts thereof, especially their sodium, magnesium, ammonium and mono-, di- and triethanolamine salts. The alkyl and acyl groups generally contain from 8 to 18, preferably from 10 to 16 carbon atoms and may be unsaturated. The alkyl ether sulphates, alkyl ether sulphosuccinates, alkyl ether phosphates and alkyl ether carboxylic acids and salts thereof may contain from 1 to 20 ethylene oxide or propylene oxide units per molecule.

Typical anionic cleansing surfactants for use in compositions of the invention include sodium oleyl succinate, ammonium lauryl sulphosuccinate, sodium lauryl sulphate, sodium lauryl ether sulphate, sodium lauryl ether sulphosuccinate, ammonium lauryl sulphate, ammonium lauryl ether sulphate, sodium dodecylbenzene sulphonate, triethanolamine dodecylbenzene sulphonate, sodium cocoyl isethionate, sodium lauryl isethionate, lauryl ether carboxylic acid and sodium N-lauryl sarcosinate.

Preferred anionic cleansing surfactants are sodium lauryl sulphate, sodium lauryl ether sulphate (n) ethylene oxide (EO), (where n is from 1 to 3), sodium lauryl ether sulphosuccinate(n)EO, (where n is from 1 to 3), ammonium lauryl sulphate, ammonium lauryl ether sulphate(n)EO, (where n is from 1 to 3), sodium cocoyl isethionate and lauryl ether carboxylic acid (n) EO (where n is from 10 to 20).

Mixtures of any of the foregoing anionic cleansing surfactants may also be suitable.

The composition can include other surfactants, for example co-surfactants.

An example of a co-surfactant is a nonionic surfactant. Representative nonionic surfactants that can be included in compositions of the invention include condensation products of aliphatic ($C_8$-$C_{18}$) primary or secondary linear or branched chain alcohols or phenols with alkylene oxides, usually ethylene oxide and generally having from 6 to 30 ethylene oxide groups.

Other representative nonionic surfactants include mono- or di-alkyl alkanolamides. Examples include coco mono- or di-ethanolamide and coco mono-isopropanolamide.

Further nonionic surfactants which can be included in compositions of the invention are the alkyl polyglycosides (APGs). Typically, the APG is one which comprises an alkyl group connected (optionally via a bridging group) to a block of one or more glycosyl groups. Preferred APGs are defined by the following formula:

wherein R is a branched or straight chain alkyl group which may be saturated or unsaturated and G is a saccharide group.

R may represent a mean alkyl chain length of from about $C_5$ to about $C_{20}$. Preferably R represents a mean alkyl chain length of from about $C_8$ to about $C_{12}$. Most preferably the value of R lies between about 9.5 and about 10.5. G may be selected from $C_5$ or $C_6$ monosaccharide residues, and is preferably a glucoside. G may be selected from the group comprising glucose, xylose, lactose, fructose, mannose and derivatives thereof. Preferably G is glucose.

The degree of polymerisation, n, may have a value of from about 1 to about 10 or more. Preferably, the value of n lies from about 1.1 to about 2. Most preferably the value of n lies from about 1.3 to about 1.5.

Suitable alkyl polyglycosides for use in the invention are commercially available and include, for example, those materials sold under the trademarks ORAMIX™ NS10 (Seppic), PLANTAREN® 1200 (Henkel), and PLANTAREN® 2000 (Henkel).

Other sugar-derived nonionic surfactants which can be included in compositions of the invention include the $C_{10}$-$C_{18}$ N-alkyl ($C_1$-$C_6$) polyhydroxy fatty acid amides, such as the $C_{12}$-$C_{18}$ N-methyl glucamides, as described for example in WO 92 06154 and U.S. Pat. No. 5,194,639, and the N-alkoxy polyhydroxy fatty acid amides, such as $C_{10}$-$C_{18}$ N-(3-methoxypropyl) glucamide.

A preferred example of a co-surfactant is an amphoteric or zwitterionic surfactant.

Examples of amphoteric or zwitterionic surfactants include alkyl amine oxides, alkyl betaines, alkyl amidopropyl betaines, alkyl sulphobetaines (sultaines), alkyl glycinates, alkyl carboxyglycinates, alkyl amphoacetates, alkyl amphopropionates, alkylamphoglycinates, alkyl amidopropyl hydroxysultaines, acyl taurates and acyl glutamates, wherein the alkyl and acyl groups have from 8 to 19 carbon atoms. Typical amphoteric and zwitterionic surfactants for use in compositions of the invention include lauryl amine oxide, cocodimethyl sulphopropyl betaine, lauryl betaine, cocamidopropyl betaine and sodium cocoamphoacetate.

A particularly preferred amphoteric or zwitterionic surfactant is cocamidopropyl betaine. A suitable example of cocamidopropyl betaine is sold under the trademark TEGO® BETAIN CK (Evonik). Mixtures of any of the foregoing amphoteric or zwitterionic surfactants may also be suitable. Preferred mixtures are those of coamidopropyl betaine with further amphoteric or zwitterionic surfactants as described above. A preferred further amphoteric or zwitterionic surfactant is sodium cocoamphoacetate.

The concentration of the surfactant in the solvent is from 0.01 to 10 wt %, preferably from 0.1 to 8 wt %, more preferably from 0.2 to 5 wt %, even more preferably from 0.5 to 2.5 wt % and most preferably from 1.0 to 2.0 wt % by weight of the total composition.

Suitable solvents include water and the lower aliphatic alcohols, particularly ethanol. More preferably the solvent is selected from water and mixtures of ethanol and water, most preferably water.

A preferred surfactant is selected from sodium lauryl ether sulphate, cocamidopropyl betaine and mixtures thereof.

A composition of the invention may contain other adjunct ingredients for enhancing performance and/or consumer acceptability. Preferred adjuncts ingredients include fragrance, dyes and pigments, pH adjusting agents, pearlescers or opacifiers, viscosity modifiers, and preservatives or anti-microbials. Each of these ingredients will be present in an amount effective to accomplish its purpose.

Preferably the composition is free from other components, especially conditioning agents and polymers other than those preferred adjunct materials, listed above, that may be polymeric.

Preferably, the compositions of the invention have a pH of from 3 to 6.

The Method

The method of the invention is a method of treating chemically damaged hair comprising the step of applying to the hair a hair treatment composition comprising (a) from 0.01 to 10 wt %, preferably from 0.5 to 2.5 wt % of surfactant in a solvent, by weight of the total composition, and (b) a mixture of amino acids, wherein the mixture of amino acids comprises glutamic acid, alanine and proline.

The chemically damaged hair is preferably selected from hair that has been subjected to treatments that modify the hair, preferably bleaching treatments, colouring treatments, straightening treatments, relaxing treatments, surfactant treatments and hot water, more preferably bleaching treatments, colouring treatments, surfactant treatments and hot water, most preferably bleaching treatments. Hair is often subjected to hot water during washing, treatment and rinsing processes. Typically, the temperature of the hot water is from 20 to 45° C. Protein and amino acid leaching from hair increases with the temperature of the water.

Preferably, the hair has been subjected to multiple damaging treatments, preferably at least 2, more preferably at least 4 damaging treatments. For example, 8 bleach treatments.

The method comprises the step of applying to the hair a composition of the invention. Preferably, application is by direct application using the hand or by spraying, most preferably spraying.

The method preferably comprises applying the composition of the invention to the hair multiple times, to give a progressive damage repair as shown by an increase in the denaturation temperature of the protein. In this way, it is possible to increase the denaturation temperature of the protein to equal to or even higher than that of virgin hair.

In the context of this invention, by virgin hair is meant hair that has not been subjected to intensive physical and/or chemical treatment, for example, bleaching, dyeing, perming, heat treatment and strong and/or prolonged exposure to solar radiation; nor displays features characteristic of damaged hair, for example, split ends and/or excessive dryness.

Virgin hair includes hair that has sustained low levels of damage during the natural hair life cycle. Sources of low level damage likely include but are not necessarily limited to brushing, combing and natural processes such as limited solar photo-degradation, for example.

The method may thus additionally comprise the step of repeating the application of the composition to the hair, preferably during a later treatment. Preferably the step of repeating the application of the composition to the hair during a later treatment is repeated 1 to 10 times, more preferably from 1 to 5 times, most preferably from 1 to 3 times.

Preferably, the composition of the invention is packaged as a spray product.

The Use

The invention provides a use of the composition of the invention to repair chemically damaged hair.

The use of the present invention provides long lasting damage repair, preferably an increase in the denaturation temperature of protein. By long lasting means that the benefit lasts for multiple treatments, preferably from 2 to 5 treatments, with a hair composition that does not comprise the amino acid mixture of the invention.

Method of Making

Each amino acid can be added separately at different stages, during the manufacture of the compositions of the invention, or the same stage, for example as a premix. Alternatively, 2 or 3 of the amino acids can be premixed before addition. They can be added, for example, as a dispersion in water or combined with a fragrance oil.

The invention will be further illustrated by the following, non-limiting Examples, in which all percentages quoted are by weight based on total weight unless otherwise stated.

EXAMPLES

Example 1—Preparation of Composition 1 in Accordance with the Invention and Comparative Composition A.

Composition 1 and A were prepared by mixing the ingredients given in Table 1 below together under ambient conditions in the amounts shown until fully dispersed.

The compositions are shown in Table 1 below.

TABLE 1

| Composition of Composition 1 and A. | | |
|---|---|---|
| | Amount (wt % of 100% active) | |
| Ingredient | Composition 1 | Comparative A |
| Water | To 100 | To 100 |
| Sodium Lauryl Ether Sulphate (SLES) | 1.6 | 1.6 |
| Glutamic acid | 0.3 | — |
| Alanine | 0.3 | — |
| Proline | 0.3 | — |

Example 2: Measurement of the Denaturation Temperatures and Change in Denaturation Temperature of Hair, Using Differential Scanning Calorimetry (DSC), to Give an Indication of the Level of Damage in Hair Treated with Composition 1 and Water Alone The internal protein of damaged hair typically has a reduced denaturation temperature compared to that of virgin hair. Damage repair is evidenced by an increase in the denaturation temperature of the internal protein of hair.

The Hair

Double-Bleached:

Hair tresses were bleached according to the following protocol. Hair was bleached twice for 30 minutes with Platine Precision White Compact Lightening Powder (L'Oreal Professionnel Paris, Paris, France) mixed with 9% cream peroxide, 30 'Vol' (Excel GS Ltd, UK) (60 g of powder mixed with 120 g cream peroxide). Hair was then washed with 14% SLES solution after the second treatment before drying.

Treatment of the Hair

Hair was given a preliminary wash as follows:

Hair was immersed in water for 30 s before being immersed in 14% aq sles solution. The hair was rubbed for 30 s, rinsed for 30 s and then treated with a non-conditioning shampoo, using 0.1 ml/1 g hair, with rubbing for 30 s and rinsing for 30 s.

The hair (double bleached) was then treated with the compositions as detailed in Example 1 above, using the following method and 5 switches for each treatment.

Hair was immersed in Compositions 1 and A for 40 min and removed, and squeezed between fingers to remove the excess.

The hair tresses were then left to dry overnight at 20° C. at 50% relative humidity.

The effect of the treatments was measured using Differential Scanning calorimetry (DSC).

The bottom 2 cm of the treated hair switches was removed using scissors. The hair was then chopped small using hair clippers. 7-10 mg of the clippings were added to the aluminium pans of the calorimeter, along with 50 μL of water. In all cases 5 hair switches were used per treatment and 1 pan was prepared per hair switch. The prepared pans were allowed to sit overnight before being run on the DSC from 100-180° C., at a rate of 5° C./min.

TABLE 5

Mean denaturation temperatures for double bleached hair treated with Composition 1 and Comparative composition A.

| Treatment | Denaturation Temperature | Standard Deviation | Statistical Grouping Student's t-Test (p value) |
|---|---|---|---|
| Composition 1 | 149.61 | 0.385 | <0.0001 |
| Composition A | 145.49 | 0.314 | <0.0001 |

It will be seen that damage repair, shown by an increase in the denaturation temperature, occurs with treatment by the compositions in accordance with the invention.

The invention claimed is:

1. A hair treatment composition comprising:
   (a) from 0.01 wt % to 10 wt % of surfactant in a solvent comprising water, by weight of the total composition, wherein the surfactant forms a dispersion of micelles in the solvent, and
   (b) a mixture of amino acids, wherein the mixture of amino acids consists of glutamic acid, alanine and proline, and wherein the mixture is free from other amino acids;
   wherein:
      the mixture of amino acids has a weight ratio of glutamic acid:alanine:proline of 2:1:1 to 1:2:1 to 1:1:2;
      the amount of the mixture of amino acids is from 0.1 wt % to 10 wt % by weight of the total hair composition; and
      the surfactant is selected from the group consisting of sodium oleyl succinate, ammonium lauryl sulphosuccinate, sodium lauryl sulphate, sodium lauryl ether sulphate, sodium lauryl ether sulphosuccinate, ammonium lauryl sulphate, ammonium lauryl ether sulphate, sodium dodecylbenzene sulphonate, triethanolamine dodecylbenzene sulphonate, sodium cocoyl isethionate, sodium lauryl isethionate, lauryl ether carboxylic acid, sodium N-lauryl sarcosinate, coco mono- or di-ethanolamide, coco mono-isopropanolamide, lauryl amine oxide, cocodimethyl sulphopropyl betaine, lauryl betaine, cocamidopropyl betaine and sodium cocoamphoacetate.

2. The hair treatment composition as claimed in claim 1, wherein the surfactant is selected from sodium lauryl ether sulphate, cocamidopropyl betaine and mixtures thereof.

3. The hair treatment composition as claimed in claim 1, wherein the surfactant is present in an amount of from 0.5 wt % to 2.5 wt % by weight of the total hair composition.

4. The composition as claimed in claim 1, wherein the composition has a pH in the range of from 3 to 6.

5. A method of treating chemically damaged hair comprising the step of applying to the hair a treatment composition comprising:
   (a) from 0.01 wt % to 10 wt % of surfactant in a solvent comprising water, by weight of the total composition, wherein the surfactant forms a dispersion of micelles in the solvent, and
   (b) a mixture of amino acids, wherein the mixture of amino acids consists of glutamic acid, alanine and proline, and is free of other amino acids;
   wherein:
      the mixture of amino acids has a weight ratio of glutamic acid:alanine:proline of 2:1:1 to 1:2:1 to 1:1:2;
      the amount of the mixture of amino acids is from 0.1 wt % to 10 wt % by weight of the total hair composition; and
      the surfactant is selected from the group consisting of sodium oleyl succinate, ammonium lauryl sulphosuccinate, sodium lauryl sulphate, sodium lauryl ether sulphate, sodium lauryl ether sulphosuccinate, ammonium lauryl sulphate, ammonium lauryl ether sulphate, sodium dodecylbenzene sulphonate, triethanolamine dodecylbenzene sulphonate, sodium cocoyl isethionate, sodium lauryl isethionate, lauryl ether carboxylic acid, sodium N-lauryl sarcosinate, coco mono- or di-ethanolamide, coco mono-isopropanolamide, lauryl amine oxide, cocodimethyl sulphopropyl betaine, lauryl betaine, cocamidopropyl betaine and sodium cocoamphoacetate.

6. The method as claimed in claim 5, wherein the chemically damaged hair is damaged by bleaching treatments, colouring treatments, straightening treatments, relaxing treatments, surfactant treatments, hot water from 20° C. to 45° C., and mixtures thereof.

7. The method as claimed in claim 5, further comprising the step of repeating the application of the composition to the hair.

8. The method as claimed in claim 7, wherein the step of repeating the application of the composition to the hair is made during a later treatment and is repeated 1 to 10 times.

9. The composition of claim 1, wherein the weight ratio of glutamic acid:alanine:proline of 1:1:1.

10. The composition of claim 1, wherein the mixture of amino acid is from 0.2 wt % to 5 wt % by total weight of the composition.

11. The composition of claim 1, wherein the mixture of amino acid is from 0.25 wt % to 2.5 wt % by total weight of the composition.

12. The composition of claim 1, wherein the composition further comprises an adjunct material selected from the group consisting of fragrances, dyes, pigments, pH adjusting agents, pearlescers, opacifiers, viscosity modifiers, preservatives, and antimicrobials.

13. The method of claim 5, wherein the composition further comprises an adjunct material selected from the group consisting of fragrances, dyes, pigments, pH adjusting agents, pearlescers, opacifiers, viscosity modifiers, preservatives, and antimicrobials.

\* \* \* \* \*